United States Patent [19]
Waters

[11] Patent Number: 4,730,624
[45] Date of Patent: Mar. 15, 1988

[54] DEVICE AND METHOD FOR DRAWING A BLOOD SAMPLE

[75] Inventor: John R. Waters, Towson, Md.

[73] Assignee: Becton, Dickinson and Company, Franklin Lakes, N.J.

[21] Appl. No.: 525,332

[22] Filed: Aug. 22, 1983

Related U.S. Application Data

[63] Continuation of Ser. No. 284,148, Jul. 16, 1981, abandoned.

[51] Int. Cl.⁴ .............................................. A61B 5/14
[52] U.S. Cl. ................................... 128/764; 604/220
[58] Field of Search ............... 128/763–767; 604/220, 221

[56] References Cited

U.S. PATENT DOCUMENTS

| | | | |
|---|---|---|---|
| 2,216,354 | 10/1940 | Pletcher | 604/220 |
| 3,536,061 | 10/1970 | Ogle | 128/764 |
| 3,577,980 | 5/1971 | Cohen | 128/765 |
| 3,885,549 | 5/1975 | Green | 128/764 X |
| 3,901,402 | 8/1975 | Ayres | 128/764 X |
| 3,930,492 | 1/1976 | Hatsuno et al. | 128/764 |
| 3,943,917 | 3/1976 | Johansen | 128/763 |
| 4,192,320 | 3/1980 | Megahed | 128/764 |
| 4,196,167 | 4/1980 | Olsen | 128/759 X |

OTHER PUBLICATIONS

Page 1151, The American V. Mueller 1980 catalog.

*Primary Examiner*—Edward M. Coven
*Attorney, Agent, or Firm*—Richard E. Brown

[57] ABSTRACT

A vacuum blood collection system is provided. The blood collection system contains an evacuated sample collection container which is open at both ends. One end of the container is closed by a self-sealing puncturable stopper adapted to be penetrated by one end of a double ended needle. The other end of the collection container is closed by a slidable sealing stopper affixed to a plunger to provide a piston assembly. The blood collection system also includes restraining means to prevent premature movement of the slidable sealing stopper and may contain a temporary seal to prevent movement of the piston assembly prior to the need for removing the blood specimen from the collection container.

2 Claims, 9 Drawing Figures

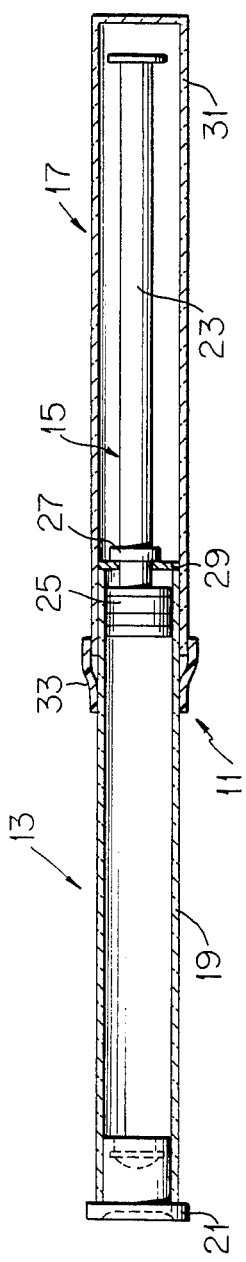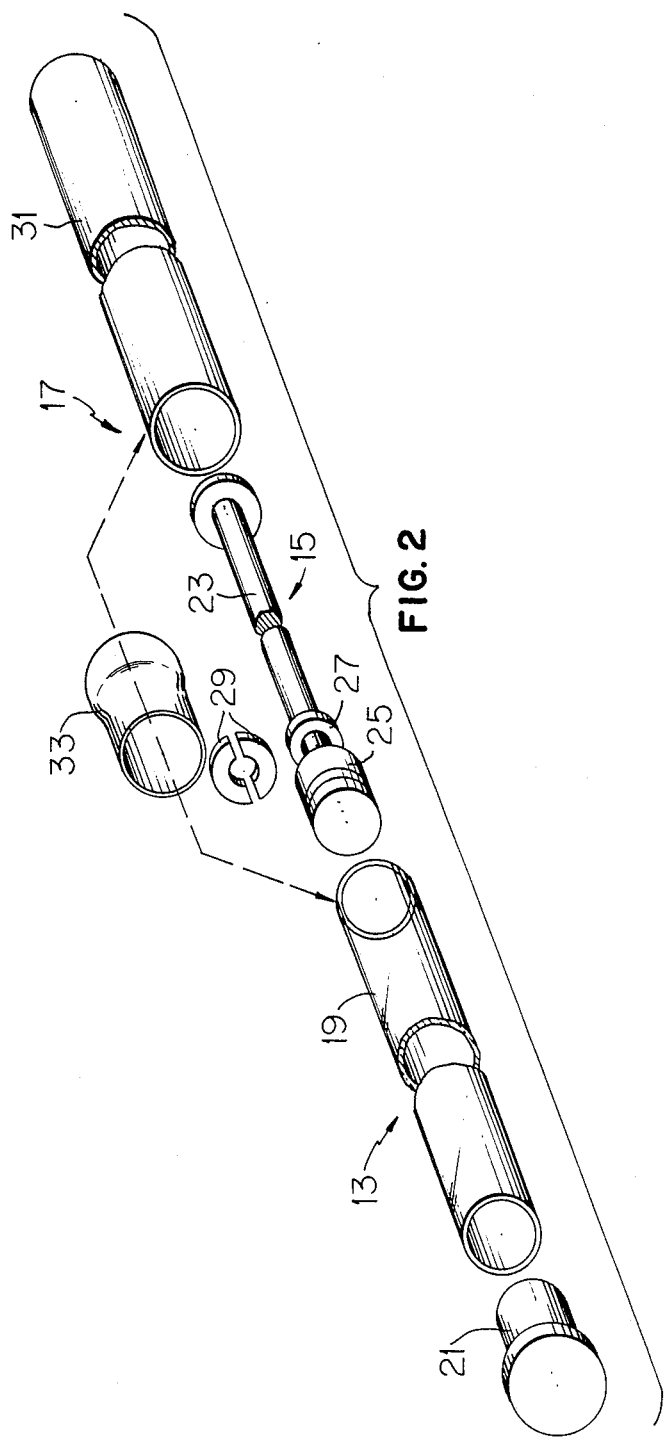

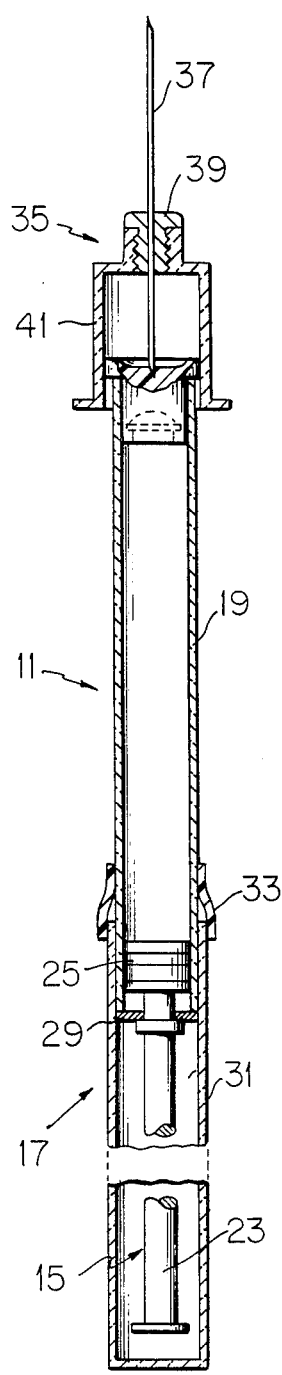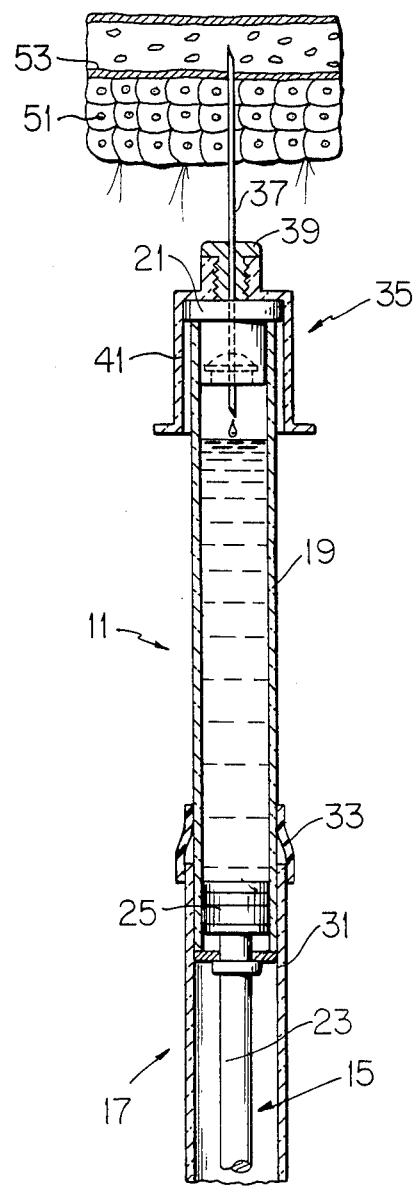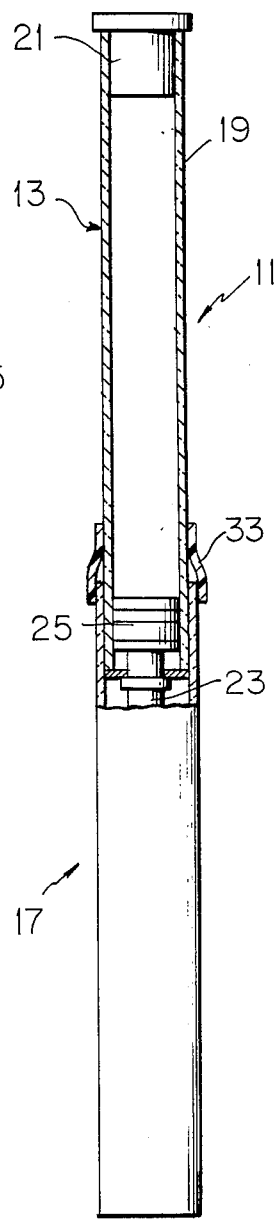

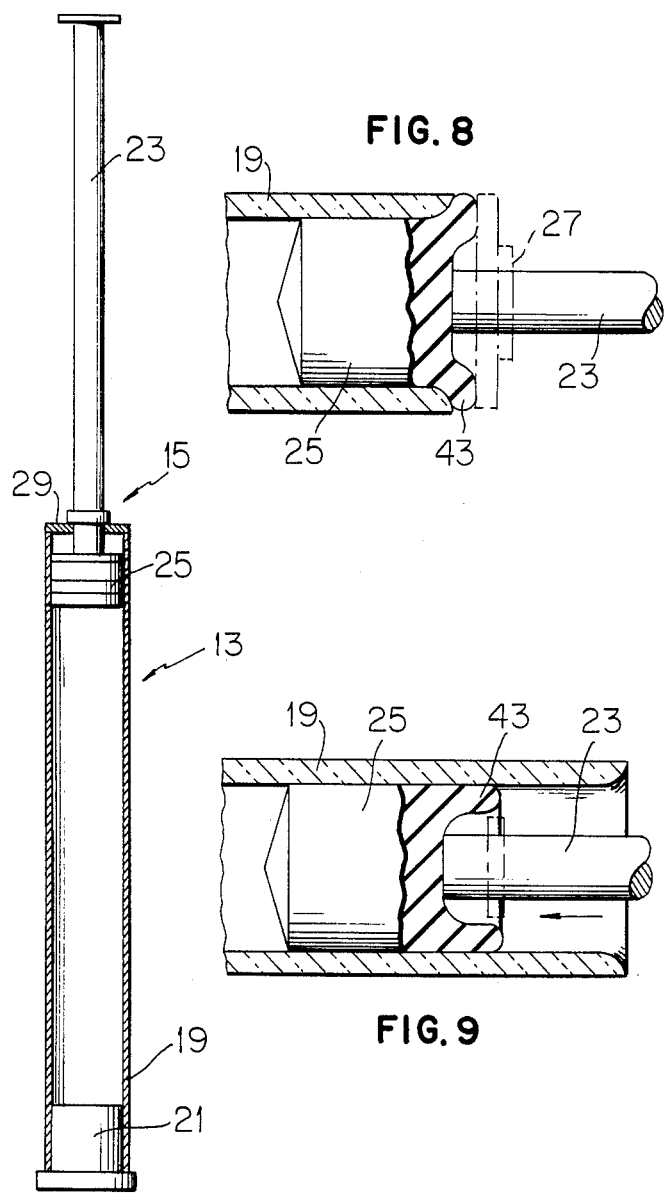
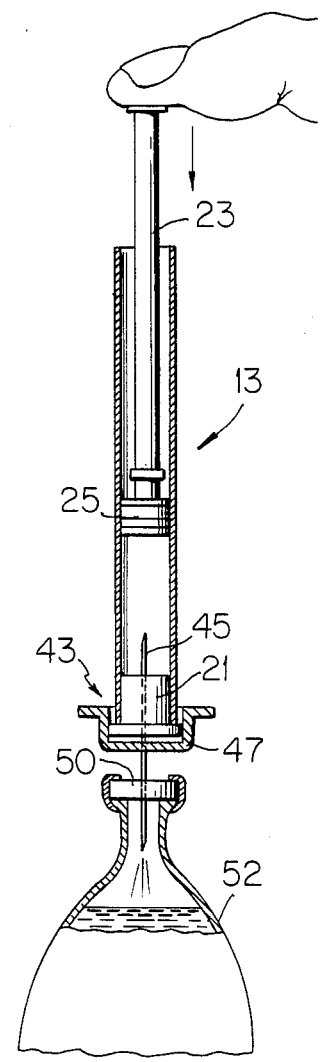
FIG. 6  FIG. 8  FIG. 9  FIG. 7

DEVICE AND METHOD FOR DRAWING A BLOOD SAMPLE

This is a continuation of application Ser. No. 284,148, filed July 16, 1981, now abandoned.

BACKGROUND OF THE INVENTION

The present invention relates generally to vacuum blood collection systems and more particularly relates to a vacuum blood collection system which facilitates drawing a blood sample and transporting the blood sample to apparatus for analysis of the blood sample.

Vacuum blood collection systems are well known and have been utilized for a number of years. A basic vacuum blood collection system is described in U.S. Pat. No. 2,460,641. The conventional system employs a double ended needle with a hub intermediate its ends which is adapted to be mounted to a holder so that one end of the needle extends forwardly from the holder and the other end of the needle extends into an interior hollow chamber in the holder. The rearward end of the holder is open to permit introduction of a stoppered evacuated tube into alignment with the rearward end of the needle so that the needle can penetrate the stopper and communicate with the interior of the container. When the forward end of the needle is introduced into a vein and the rearward end of the needle is in communication with the evacuated tube, the pressure differential between the venous pressure and the evacuated tube causes blood to flow into the tube for collection of a blood sample. U.S. Pat. Nos. 3,965,889; 3,890,955 and 3,817,240 are further examples of basic vacuum blood collection systems.

Various improvements have been made to vacuum blood collection systems, such as by providing valves to shut off flow from the vein while evacuated collection tubes are interchanged for purposes of providing a plurality of samples. Examples of this type of improvement are described in U.S. Pat. Nos. 3,494,352 and 3,469,572.

Further improvements in the basic vacuum blood collection system have utilized various means to indicate correct positioning of the device in the vein. Examples of this type of improvement are described in U.S. Pat. Nos. 3,942,514; 3,886,930 and 3,817,240.

Another improvement is the provision of indexing means on the holder and stopper tube for purposes of indicating the relative position of the stopper and needle. U.S. Pat. No. 3,366,103 describes this type of improvement. A still further improvement of this type is described in U.S. Pat. No. 4,154,229.

While the above described vacuum blood collection systems and improvements have been highly successful there is a need for providing an improved device and method for transferring the collected blood sample from the vacuum blood collection system into self-contained culture media vials. Such self-contained culture media vials are well known in blood analysis technology and require the penetration of a rupturable seal by a needle for injection of the blood sample into the vial. It would be desirable to provide a vacuum blood collection system which is capable of collecting the blood sample and transferring the blood sample into a self-contained culture media vial or other receptacle without use of an intermediate transfer tube.

SUMMARY OF THE INVENTION

It is a principal object of the present invention to provide a vacuum blood collection system which utilizes the accepted and conventional method of collecting blood specimens; that is, a double ended needle, a holder for the needle and an evacuated stoppered tube, and additionally, provides structure permitting the transfer of the collected blood specimen into a stoppered vial or other receptacle without requiring intermediate transfer of the collected blood specimen into a transfer tube.

A further objective is to provide a conventional evacuated stoppered tube with a rearwardly mounted slidable stopper which is secured in place until it is required to remove the blood specimen from the tube.

A further objective is to provide a conventional evacuated stoppered tube with a piston assembly temporarily secured in place at one end of the stoppered tube which is adapted to remove a blood specimen from the stoppered tube after collection thereof.

It is also contemplated that a double ended needle can be used, in combination with the piston assembly, to effect transfer of the blood specimen from the evacuated stoppered tube into a stoppered vial or other receptacle. The double ended needle can be formed of two separate needle portions mounted in a hub having a passageway therethrough so that one needle portion extends from one end of the hub and the other needle portion extends from the other end of the hub.

The vacuum blood collection system of the invention, including the piston assembly and slidable stopper, is inexpensive and easy and efficient to utilize thereby maintaining a low cost design for the system which is adaptable to mass production.

In summary, a vacuum blood collection system is provided in accordance with the invention which is adapted to be used with a double ended needle open at both ends and having a passageway therethrough. The same double ended needle or a separate double ended needle can be used to evacuate the blood specimen collected by the blood collection system. An evacuated sample collection container is provided which is open at both ends. One end is closed by a self-sealing puncturable stopper adapted to be penetrated by the rear end of the double ended needle to provide fluid communication between the passageway through the double ended needle and the interior of the sample collection container. The other end of the collection container is closed by a slidable seal affixed to a plunger to provide a piston assembly. A temporary seal is used with some embodiments of the invention to restrain movement of the piston assembly prior to the need for removing the blood specimen from the collection container. With the temporary seal removed and a double ended needle in fluid communication with the interior of the sample collection container, the piston assembly is used to remove the blood specimen from the sample collection container into a stoppered or open mouthed receptacle.

BRIEF DESCRIPTION OF THE DRAWINGS

FIG. 1 is a side elevation view of the blood collection system of the invention.

FIG. 2 is an exploded sectional perspective view of the blood collection system of the invention;

FIG. 3 is a sectional elevation view in coupled relative position prior to venipuncture;

FIG. 4 is a sectional elevation view showing the components of the system in relative coupled position after a successful venipuncture;

FIG. 5 is a sectional elevational view showing the components of the system in relative position for transfer of the sample to an analysis laboratory;

FIG. 6 is a sectional elevation view showing the components of the system in operative position for removal of the blood specimen;

FIG. 7 is a sectional elevation view showing components of the system in operative position relative to a stoppered receptacle for transfer of the blood specimen to the receptacle;

FIG. 8 is a further embodiment of the slidable stopper means; and

FIG. 9 is a sectional elevation view of the stopper means of FIG. 8 showing the stopper in operative position.

DETAILED DESCRIPTION OF THE INVENTION

The depicted embodiment of the invention is of the type commonly used for collection of a blood sample from the vein of a patient. While the present invention is particularly useful for that purpose, it is also contemplated that the structure is equally useful in other environments where samples are being transferred from one vessel to the other and where pressure differential conditions between the vessels exist. Additionally, it is contemplated that reactive and stabilizing components can be placed within the sample collection container for reaction with the sample prior to removal of the sample from the container. For example, resins of various types of anticoagulants could be placed within a sample collection container prior to use of the container to extract a sample.

The components of the blood collection system 11 are shown in FIG. 1 and the component assemblies are shown in the exploded view of FIG. 2. The blood collection system 11 comprises a container assembly 13, a piston assembly 15 and a cover assembly 17.

Container assembly 13 includes a collection tube 19 which is open at both ends. A first end of collection tube 19 is sealed with stopper 21. The piston assembly 15 includes means, such as syringe seal 25, for sealing a second end of collection tube 19. The piston assembly 15 also includes a piston rod 23 and may include a collet 27 and a retaining clip 29. The retaining clip 29 is separable from the piston rod 23. When in place, the retaining clip 29 bears against the end of collection tube 19 and prevents the piston rod 23 from sliding into collection tube 19 when collection tube 19 is evacuated. The cover assembly 17 includes a hollow tube protective cover 31 which is sealed at one end. Protective cover 31 fits over piston rod 23 to prevent accidental movement of piston rod 23 into collecting tube 19 until desired. A security seal 33 is fastened around protective cover 31 to prevent removal of protective cover 31 until desired. Security seal 33 is preferably a plastic band of the tear off type.

The various components of the blood collection system of the invention are fabricated from conventional suitable materials well known in the art. The collection tube 19 for example, may be glass or a rigid polymeric material such as polystyrene and polypropylene. The stopper 21 and the syringe seal 25 are preferably made from an elastomeric material capable of slight deformation to provide a gas tight seal when in place within collection tube 19. The piston rod 23 may be made from any rigid material, including metal and rigid polymeric materials. The protective cover 31 is preferably made from a clear polymeric material, such as polyethylene and polypropylene. The protective seal 33 is preferably a flexible film of a polymeric material, such as a polyester, which is preferably affixed in place around the protective cover 31 with and adhesive or by heat shrinking.

In operation, as shown in FIGS. 3 and 4, a needle assembly 35 is coupled with the blood collection system 11 to effect venipuncture. The needle assembly 35 includes a double ended needle 37, a hub 39 and a hollow tubular body 41. The hub 39 has a threaded portion which screws into a threaded opening of the hollow tubular body 41 to complete the needle assembly 35.

Thereafter, the blood collection system 11 in the condition shown in FIG. 3 is maneuvered in position so that the exposed end of the needle is introduced into the vein of a patient. A successful introduction of the needle into the vein of a patient is shown in FIG. 4 where the tip of the exposed needle has passed through subcutaneous tissue 51 and entered vein 53. The system is dimensioned so that the hollow tubular body 41 can be maneuvered onto collection tube 19 to a position wherein the outward pointed end of the double ended needle 37 can penetrate the vein 53 while the rearward pointed end of the double ended needle 37 will not have penetrated through the stopper 21 into the interior of the blood collection system as shown in FIG. 3. After verification of a successful venipuncture has been accomplished; such as by use of the needle assembly described in U.S. Pat. No. 4,154,229, the container assembly 13 can be pushed all the way into the hollow tubular body 41. This permits the rearward end of the double ended needle 37 to penetrate stopper 21 completing fluid communication between the vein 53 and the interior of tube 19. The pressure differential between the partially or fully evacuated tube 19 and the venous pressure of vein 53 causes blood to flow from the vein into the tube for collection of the blood sample.

Blood collects within tube 19 until pressure is equalized between the vein and the interior of the collection tube whereupon the blood flow will stop. Thereafter, as shown in FIG. 5, the pointed end of the double ended needle assembly 35 is removed from the blood collection system 11 and the blood collection system 11 is ready for transport to a desired location. When it is desired to remove the blood sample from the container assembly 13, the temporary seal 33 is removed and the protective cover is removed from the end of the piston assembly 15. This ready position is shown in FIG. 6. A venting assembly 44 is then inserted into the stopper 21. The venting assembly 44 comprises a double ended needle 45 and a holder 47. The exposed end of double ended needle 45 is inserted into the stopper 50 of a receptacle 52. The blood sample is removed from the collection tube 19 by depressing the syringe rod 23 to slide the syringe seal 25 throughout the length of the collection tube 19 in the usual manner of removing contents from a syringe.

An alternative embodiment of the syringe seal 25 is shown in FIG. 8. As shown in FIG. 8 the syringe seal 25 is fabricated from an elastomeric material and provided with compression ring 43. Use of this ring configuration of the syringe seal 25 provides a compression seal when the tube 19 is evacuated. The compression ring 43 is caused to compress against the end of tube 19 to effect a compression seal. This permits evacuation of collection tube 19 without the need for providing a retaining clip 29 and a collet 27 (shown in phantom outlined in FIG. 8) to prevent sliding of the syringe seal 25 within tube 19 prematurely. It may still be desirable, as a safety measure, to provide the retaining clip 29 and the collet 27 for positive prevention of any premature movement of syringe seal 25 within tube 19. As shown in FIG. 9 the compression ring 43 is deformed when sufficient force is applied to the piston rod 23 to permit the syringe seal 25 to slide within collection tube 19.

Although several preferred embodiments have been disclosed and described in detail herein, it should be understood that the present invention is not limited thereby and the scope of the invention is determined by that of the appended claims.

What is claimed is:

1. A blood collection and transport system comprising:
   (a) a preevacuated sample collection and transport container having a first forward open end and a second rearward open end;
   (b) a first self-sealing puncturable stopper affixed to said first end of said container, said stopper being penetrable by one end of a double ended needle to provide fluid communication between a passageway through the needle and the interior of the container;
   (c) a second sealing stopper for said second end of said container;
   (d) a piston assembly comprising a piston rod affixed to said second sealing stopper for said second end of said container, said second stopper being slidable within said sample collection container upon application of force to said piston rod;
   (e) a collet affixed to said piston rod and a retaining clip removably affixed to said piston rod and positioned between said collet and the end of said collection container whereby said collet bears upon said retaining clip, said collet and retaining clip restraining said second stopper from movement into said preevacuated sample collection container until a sample collected therein is to be discharged; and
   (f) a protective cover removably fitted over said piston rod and a removable seal fastened around said protective cover to prevent removal of said protective cover until actuation of said piston rod is required.

2. A blood collection and transport system comprising:
   (a) a preevacuated sample collection and transport container having a first forward open end and a second rearward open end;
   (b) a first self-sealing puncturable stopper affixed to said first end of said container, said stopper being penetrable by one end of a double ended needle to provide fluid communication between a passageway through the needle and the interior of the container;
   (c) a second sealing stopper for said second end of said container, said second stopper including a compression ring adapted to bear against the end of said sample collection container prior to movement of said second stopper within said collection container by actuation of said piston rod, said compression ring thereby restraining said second stopper from movement into said preevacuated sample collection container until a sample collected therein is to be discharged;
   (d) a piston assembly comprising a piston rod affixed to said second sealing stopper, said second stopper being slidable within said sample collection container upon application of force to said piston rod; and
   (e) a protective cover removably fitted over said piston rod and a removable seal fastened around said protective cover to prevent removal of said protective cover until actuation of said piston rod is required.

* * * * *